United States Patent [19]

Harris et al.

[11] Patent Number: 4,622,986
[45] Date of Patent: Nov. 18, 1986

[54] DENTAL FLOSS KNOT TYING DEVICE

[76] Inventors: Robert W. Harris, 625 NW. 41st St., Seattle, Wash. 98107; William R. Weber, 4200-50th Ave. NE., Seattle, Wash. 98105

[21] Appl. No.: 794,700

[22] Filed: Nov. 4, 1985

[51] Int. Cl.[4] .............................................. A61C 15/00
[52] U.S. Cl. .................................................. 132/92 R
[58] Field of Search ................... 132/92 R, 92 A, 93, 132/91

[56] References Cited

U.S. PATENT DOCUMENTS

| 1,608,212 | 11/1926 | Hochstadter | 132/92 R |
| 3,393,687 | 7/1968 | Whitman | 132/91 |
| 3,747,611 | 7/1973 | Bennington | 132/91 |
| 3,901,251 | 8/1975 | Johnston | 132/91 |
| 3,924,647 | 12/1975 | Lindblad | 132/92 R |
| 4,434,807 | 3/1984 | Huskey | 132/92 R |

Primary Examiner—John J. Wilson

[57] ABSTRACT

A device to aid in the tying of dental floss having a compartment to retain the dental floss which can be withdrawn, doubled back, wound around a conical member, passed through a groove and slot and threaded back through, and slipped off of the conical member forming a convenient loop used to more easily floss the teeth.

2 Claims, 9 Drawing Figures

DENTAL FLOSS KNOT TYING DEVICE

BACKGROUND OF THE INVENTION

1. Field of invention

This invention relates to devices which make it easier for the user to floss the teeth.

2. Prior Art

The awkwardness of the present method of flossing the teeth has been recognized for many years. Many devices have been patented to alleviate this situation. Most of the devices, however, deal with a method of holding the floss, in a device, while flossing the teeth, thus avoiding the discomfort of the floss wound around the fingers and to keep the fingers directly out of the mouth. None of these devices have "caught on," perhaps because they require too much time to attach the floss to them.

The present invention takes a different approach to the difficulty in flossing the teeth. It is recognized that the hands and fingers are better able to hold and guide the floss; however, the present method of wrapping the floss around the fingers is awkward and difficult for the old, young, or those with hand problems. Floss in a loop of approximately three inches in diameter is easily held, making flossing the teeth much less difficult. At the present time floss is sold wound on spools and to get a loop one must tie one's own. Dental floss is relatively thin and unruly, making it time-consuming to knot. The present invention makes tying dental floss into loops easier; it will encourage more people to floss their teeth. Anyone with a reasonable amount of dexterity should be able to use the present invention.

SUMMARY OF THE INVENTION

The present invention applies to devices which make flossing the teeth easier, particularly to a device which can be used to knot dental floss into convenient loops. The device is self-contained with no moving parts: it has a compartment for stowing the dental floss, which can be drawn out, doubled, and wound around a hollow frustum of a cone, passed through a groove in the cone, then through a slot, to the reverse side of the body, to which the cone is attached, and brought up through and slipped off of the cone to create a knot, thus leaving the dental floss in a convenient loop which be cut off and used.

DESCRIPTION OF INVENTION

Figure 3:
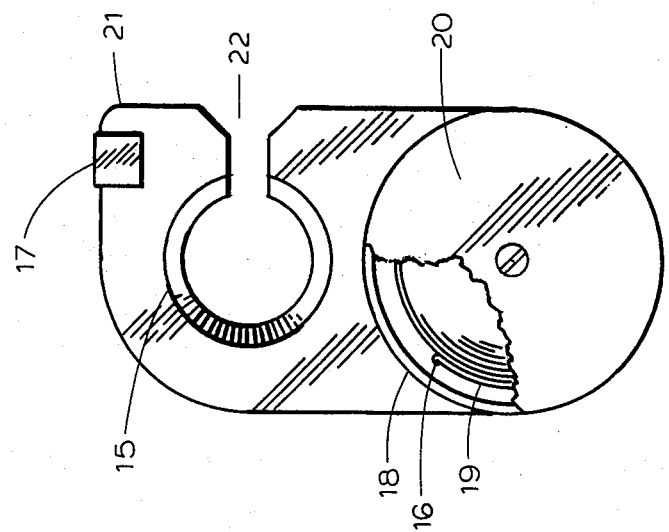
FIGS. 1 through 3 show the front, side and reverse views with a hollow section of the cone 15 on the front side, with a hole 16 in the body for passage of the dental floss 19 and a dental floss cutter 17. The reverse side shows the dental floss storage 18 with coiled dental floss 19 shown in a cutaway of the cover 20. The above are attached to a body 21, which has a slot 22 for passage of the dental floss 19, which aligns with a groove in the cone 15.
Figure 2:
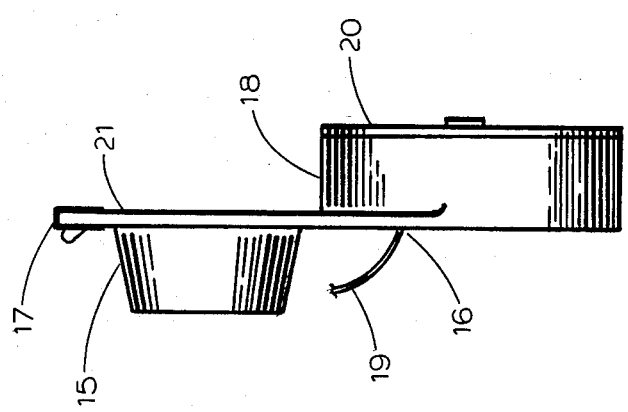
Figure 1:
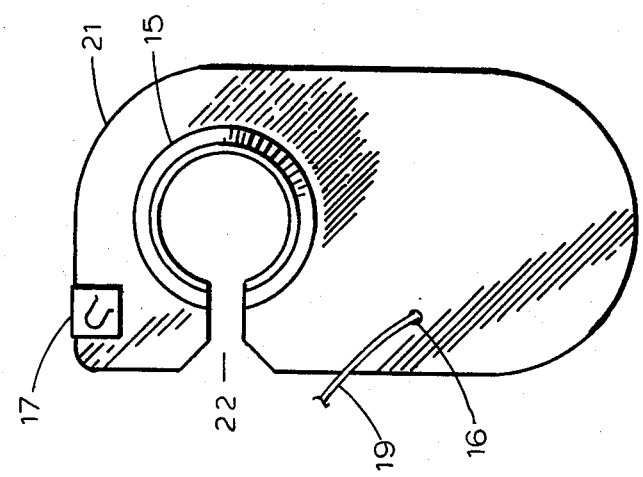
Figure 8:
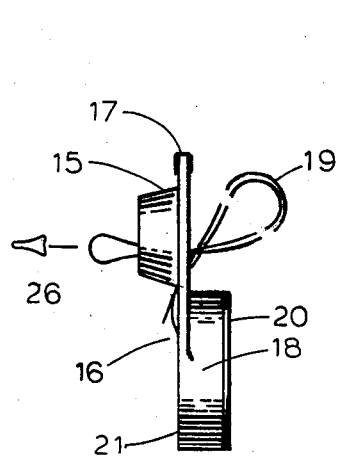
FIGS. 5 through 9 depict a sequence of steps in forming a loop in the dental floss 19.
Figure 9:
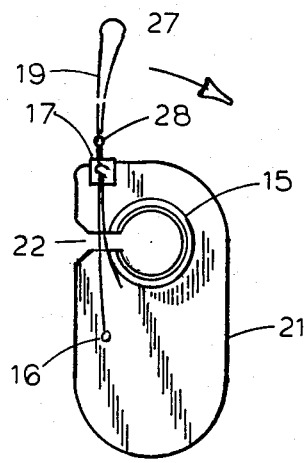
Figure 7:
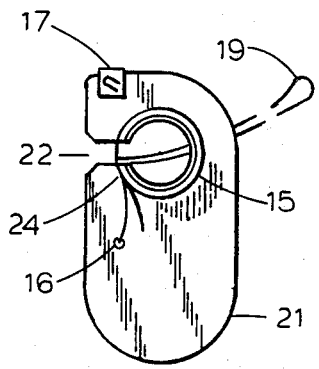
Figure 6:
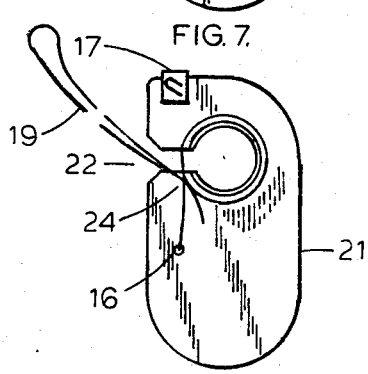
Figure 5:
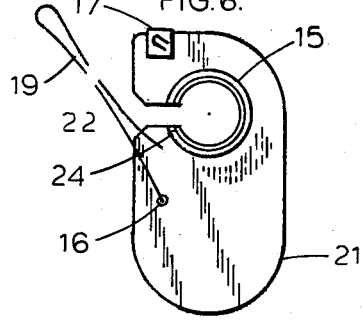
Figure 4:
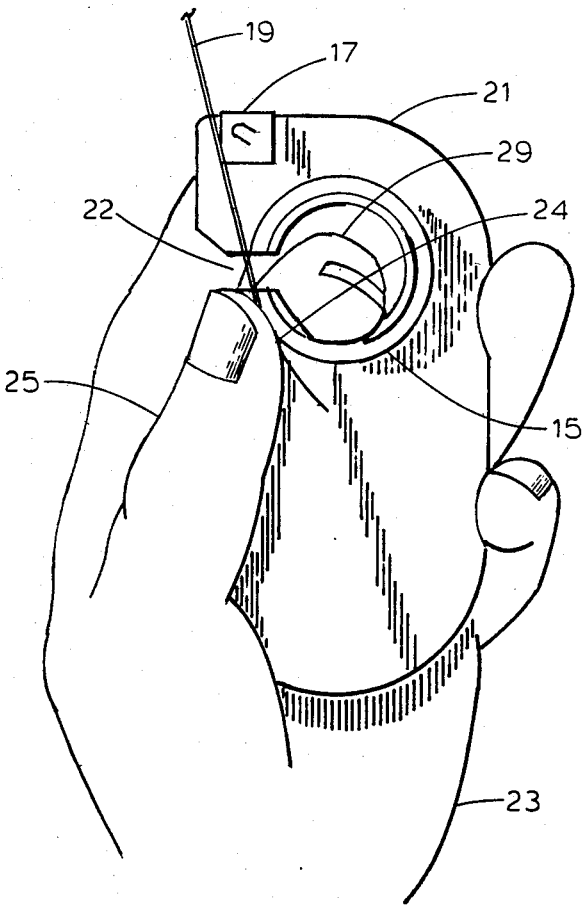
FIG. 4 is a sketch of the device positioned in the palm of the hand 23 ready to begin forming a loop of dental floss 19.

The drawings illustrate by way of example, not by way of limitation, one form of the preferred embodiment of the present invention, wherein are reference numerals to designate parts in the several views. With reference to FIG. 1, the present invention's (hereinafter called device) front side is shown, with a hollow frustum of a cone 15, a dental floss cutter 17 and a hole 16 in the body 21. The frustum of a cone 15 is mounted on the body 21 concentric with a hole in the body 21, with the grove in the cone 15 aligned with a slot 22 in the body 21. Also shown on the front side of the body 21 is a hole 16 through which the dental floss 19 is threaded. FIG. 2 and 3 show the dental floss compartment 18, its cover 20 and a roll of dental floss 19. Referring to FIG. 4, the device is shown positioned in the palm of the hand 23 in a suggested position with the second finger 29 free to enter the cone 15 from the reverse side. The position of the thumb 25 rests against the cone 15 at 24. FIGS. 5 through 9 show the sequence used to form a dental floss 19 loop as shown in FIG. 9 at 27. Referring to FIG. 5, the dental floss 19 is withdrawn from the hole 16 to a length of approximately eighteen inches and doubled back to 24 where both strands are restrained by the thumb. FIG. 6 shows the dental floss 19 wrapped around the cone 15 in the clockwise direction. FIG. 7 shows the dental floss 19 fed through the slot 22 in the body 21 to the reverse side of the device. FIG. 8 shows the dental floss 19 fed through the cone 15 toward the front side at 26. This movement can be aided by the middle finger 29. During all of the movements the dental floss 19 is kept rather taut to insure that it will not come off of the cone 15. After the dental floss 19 is fully pulled through the hole in 15, the portion around the cone 15 will slide off, forming a knot in the dental floss. FIG. 9 shows the last step with the floss 19 formed into a loop at 27 and ready for cutoff by the cutter 17. To cut off the dental floss loop, the knot 28 is positioned above the cutter 17 and then pulled to the right as shown by the arrow.

For this and other reasons, it can be stated that, while the preferred embodiments of the invention have been herein described and illustrated, it should be understood that various modifications and alterations may be made without departing from the spirit of the invention or scope defined by the appended claims.

Now therefore we claim:

1. A device to aid in the tying of dental floss comprising:
   a. a dental floss storage compartment attached to a body;
   b. said body having a hole with a slot extending to an outside edge;
   c. a hollow tubular member, with an open groove, mounted on the body concentric to the hole with the groove aligned with the slot in the body;
   d. a dental floss cutting means; and,
   e. dental floss in said storage compartment, whereby a length of dental floss can be withdrawn from the storage compartment, doubled back, wrapped around the hollow tubular member, then through the slot to the reverse side of the body and inserted, from the reverse side, through the hollow tubular member to tie a knot forming a loop of a convenient size for flossing the teeth.

2. A device to aid in the tying of dental floss as claimed in claim one wherein said hollow tubular member is a hollow frustum of a cone, attached to the body such that the dental floss will readily slip off as the knot is forming.

* * * * *